(12) United States Patent
Lehman, Jr. et al.

(10) Patent No.: US 10,966,736 B2
(45) Date of Patent: Apr. 6, 2021

(54) SPINAL IMPLANT SYSTEM AND METHODS OF USE

(71) Applicant: Warsaw Orthopedic, Inc., Warsaw, IN (US)

(72) Inventors: Ronald A. Lehman, Jr., Tenafly, NJ (US); William Alan Rezach, Covington, TN (US); Rodney Ray Ballard, Lakeland, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/985,410

(22) Filed: May 21, 2018

(65) Prior Publication Data
US 2019/0350600 A1 Nov. 21, 2019

(51) Int. Cl.
| | | |
|---|---|---|
| *A61B 17/17* | (2006.01) | |
| *A61B 34/00* | (2016.01) | |
| *A61B 34/20* | (2016.01) | |
| *A61B 34/30* | (2016.01) | |
| *A61F 2/46* | (2006.01) | |

(Continued)

(52) U.S. Cl.
CPC .......... *A61B 17/1757* (2013.01); *A61B 34/20* (2016.02); *A61B 34/30* (2016.02); *A61B 34/70* (2016.02); *A61F 2/4611* (2013.01); *A61B 17/86* (2013.01); *A61B 2034/107* (2016.02);
(Continued)

(58) Field of Classification Search
CPC ..... A61B 17/1757; A61B 6/583; A61B 34/72; A61B 34/70; A61B 34/30; A61B 34/20; A61B 34/25; A61B 19/5244; A61B 2034/2055; A61B 2034/2072; A61B 2034/254; A61B 2034/107; A61B 2034/2051; A61B 2034/102; A61B 2019/5251; A61B 2019/502; A61B 2019/507; Y10S 606/907; Y10S 606/909; Y10S 606/914; A61F 2/4611; A61F 2/442; A61F 2/4455; A61F 2002/2839; A61F 2002/4627; A61F 2002/4632
USPC .......... 600/417, 421, 427, 429; 606/90, 130, 606/907, 909, 912, 97, 914, 96, 99, 86 A, 606/246–289, 300–328; 382/128, 173, 382/209, 294

See application file for complete search history.

(56) References Cited

U.S. PATENT DOCUMENTS

| | | |
|---|---|---|
| 5,595,193 A | 1/1997 | Walus et al. |
| 5,649,926 A | 7/1997 | Howland |

(Continued)

FOREIGN PATENT DOCUMENTS

| | | |
|---|---|---|
| JP | 2013526905 A | 6/2013 |
| KR | 1020110033199 A | 3/2011 |

OTHER PUBLICATIONS

International Search Report and Written Opinion of the International Searching Authority, European Patent Office, PCT/US2019/031950, dated Sep. 25, 2019.

*Primary Examiner* — Pedro Philogene
(74) *Attorney, Agent, or Firm* — Sorell, Lenna & Schmidt, LLP (57) ABSTRACT

A surgical device has a shaft including a proximal portion and a distal portion being disposable with a surgical robot guide to engage vertebral tissue. The proximal portion defines a detectable marker and is connectable with at least one surgical instrument for manipulating the vertebral tissue. Systems, surgical instruments, spinal implants, constructs and methods are disclosed.

20 Claims, 8 Drawing Sheets

(51) Int. Cl.
*A61B 17/86* (2006.01)
*A61B 34/10* (2016.01)

(52) U.S. Cl.
CPC ............... *A61B 2034/2055* (2016.02); *A61B 2034/2072* (2016.02); *A61F 2002/4632* (2013.01)

(56) References Cited

U.S. PATENT DOCUMENTS

| | | | |
|---|---|---|---|
| 6,348,058 | B1 | 2/2002 | Melkent et al. |
| 6,796,988 | B2 * | 9/2004 | Melkent ............. A61B 17/1757 |
| | | | 600/429 |
| 6,980,849 | B2 | 12/2005 | Sasso |
| 7,083,621 | B2 * | 8/2006 | Shaolian ............. A61B 17/1671 |
| | | | 606/256 |
| 7,273,481 | B2 * | 9/2007 | Lombardo ......... A61B 17/8042 |
| | | | 606/86 A |
| 7,569,058 | B2 * | 8/2009 | Zwimmann ........ A61B 17/1633 |
| | | | 606/80 |
| 7,655,008 | B2 | 2/2010 | Lenke et al. |
| 7,660,623 | B2 | 2/2010 | Hunter et al. |
| 7,794,464 | B2 | 9/2010 | Bridwell et al. |
| 7,881,770 | B2 | 2/2011 | Melkent et al. |
| 7,998,062 | B2 | 8/2011 | Gilboa |
| 8,043,345 | B2 | 10/2011 | Carl et al. |
| 8,057,407 | B2 * | 11/2011 | Martinelli ............. A61B 34/20 |
| | | | 600/407 |
| 8,105,339 | B2 | 1/2012 | Melkent et al. |
| 8,277,490 | B2 | 10/2012 | Freemen et al. |
| 8,335,553 | B2 | 12/2012 | Rubner et al. |
| 8,571,638 | B2 * | 10/2013 | Shoham ............. A61B 17/1757 |
| | | | 600/427 |
| 8,696,685 | B2 | 4/2014 | Gilboa |
| 8,763,499 | B2 * | 7/2014 | Dahners ............. A61B 17/8615 |
| | | | 411/408 |
| 8,801,601 | B2 | 8/2014 | Prisco et al. |
| 8,842,893 | B2 * | 9/2014 | Teichman ............ G06K 9/6202 |
| | | | 382/128 |
| 10,136,902 | B2 * | 11/2018 | Farris ................. A61B 17/1655 |
| 2005/0021037 | A1 | 1/2005 | McCombs et al. |
| 2005/0027832 | A1 | 2/2005 | Bavaria et al. |
| 2007/0055291 | A1 | 3/2007 | Birkmeyer et al. |
| 2007/0213715 | A1 | 9/2007 | Bridwell et al. |
| 2011/0160861 | A1 | 6/2011 | Jimenez et al. |
| 2011/0172714 | A1 | 7/2011 | Boachie-Adjei et al. |
| 2011/0172718 | A1 | 7/2011 | Felix et al. |
| 2011/0257690 | A1 | 10/2011 | Rezach |
| 2013/0345718 | A1 * | 12/2013 | Crawford ............. A61B 17/025 |
| | | | 606/130 |
| 2014/0114414 | A1 | 4/2014 | Abdou et al. |
| 2015/0018886 | A1 * | 1/2015 | Ali ......................... A61F 2/4455 |
| | | | 606/279 |
| 2016/0007983 | A1 | 1/2016 | Frey et al. |
| 2016/0022438 | A1 | 1/2016 | Lamborne et al. |
| 2016/0058477 | A1 | 3/2016 | Smith |
| 2016/0067056 | A1 | 3/2016 | Armstrong et al. |
| 2017/0035482 | A1 * | 2/2017 | Magee ................. A61B 17/686 |
| 2018/0256259 | A1 * | 9/2018 | Crawford ............. A61B 34/10 |

* cited by examiner

SPINAL IMPLANT SYSTEM AND METHODS OF USE

TECHNICAL FIELD

The present disclosure generally relates to medical devices for the treatment of musculoskeletal disorders, and more particularly to a surgical system and method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, interbody devices can be employed with spinal constructs, which include implants such as bone fasteners and vertebral rods to provide stability to a treated region. These implants can redirect stresses away from a damaged or defective region while healing takes place to restore proper alignment and generally support the vertebral members. During surgical treatment, one or more rods and bone fasteners can be delivered to a surgical site. Surgical instruments are employed, for example, to engage the fasteners for attachment to the exterior of two or more vertebral members. This disclosure describes an improvement over these prior technologies.

SUMMARY

In one embodiment, a surgical device for treating a spine is provided. The surgical device has a shaft including a proximal portion and a distal portion being disposable with a surgical robot guide to engage vertebral tissue. The proximal portion defines a detectable marker and is connectable with at least one surgical instrument for manipulating the vertebral tissue. Systems, surgical instruments, spinal implants, constructs and methods are disclosed.

In one embodiment, a method for treating a spine is provided. The method comprises the steps of: engaging a distal portion of a surgical device with vertebral tissue via robotic guidance, the distal portion including a tap and a proximal portion including a detectable marker; connecting a surgical instrument with the proximal portion; and manipulating the surgical instrument to rotate a first vertebra of the vertebral tissue relative to a second vertebra.

In one embodiment, a surgical instrument is provided. The surgical instrument includes a shaft including a distal portion having a threaded tap and a proximal portion having a radiographically detectable marker. The distal portion is disposable with a surgical robot guide to engage vertebral tissue. The proximal portion is connectable with a distractor.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system are discussed in terms of medical devices for the treatment of musculoskeletal disorders and more particularly, in terms of a surgical system and a method for treating a spine. In some embodiments, the present surgical system includes a surgical device comprising one or more surgical instruments and/or spinal implants that provide marking and guidance for disposal of components of the present surgical system with vertebral tissue. In some embodiments, the surgical device provides marking and guidance for a selected position of vertebrae for implant of a pedicle screw. In some embodiments, the surgical device provides vertebral manipulation to treat spinal disorders, for example, to manage lordosis and/or kyphosis restoration. In some embodiments, the surgical device provides distraction and/or compression of vertebral tissue. In one embodiment, the systems and methods of the present disclosure are employed with a spinal joint fusion, for example, with a cervical, thoracic, lumbar and/or sacral region of a spine.

In some embodiments, the present surgical system includes a surgical device comprising one or more surgical instruments and/or spinal implants that include a pedicle marker and a tap. In some embodiments, the pedicle marker includes a cannulated tap used to mark a location and a trajectory of a pedicle screw placement. In some embodiments, the pedicle marker is employed with surgical navigation. In some embodiments, the pedicle marker is employed to distract vertebrae. In some embodiments, the pedicle marker comprises a provisional instrument.

In some embodiments, the present surgical system includes a surgical device comprising one or more surgical instruments that include a pedicle screw marker utilized to mark a location and trajectory of a pedicle screw placement via surgical navigation or surgical guidance. In some embodiments, the pedicle screw marker is configured for connection with a surgical tool to facilitate manipulation of vertebrae. In some embodiments, the pedicle screw marker is configured for connection with a surgical tool, such as, for example, a distractor to distract vertebrae.

In some embodiments, the present surgical system includes a surgical device comprising one or more surgical instruments and/or spinal implants that include a pedicle marker. In some embodiments, the shaft is configured as a tap. In some embodiments, the pedicle marker is configured to distract tissue during a transforaminal lumbar interbody fusion (TLIF) procedure. In some embodiments, the present surgical system includes a surgical device that is employed with a method of treating a spine including the step of placing the surgical device under robotic guidance. In some embodiments, the pedicle marker has a solid shaft. In some embodiments, the pedicle marker has a cannulated shaft.

In some embodiments, the system of the present disclosure may be employed to treat spinal disorders such as, for example, degenerative disc disease, disc herniation, osteoporosis, spondylolisthesis, stenosis, kyphosis, scoliosis and other curvature abnormalities, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or anterolateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 1:
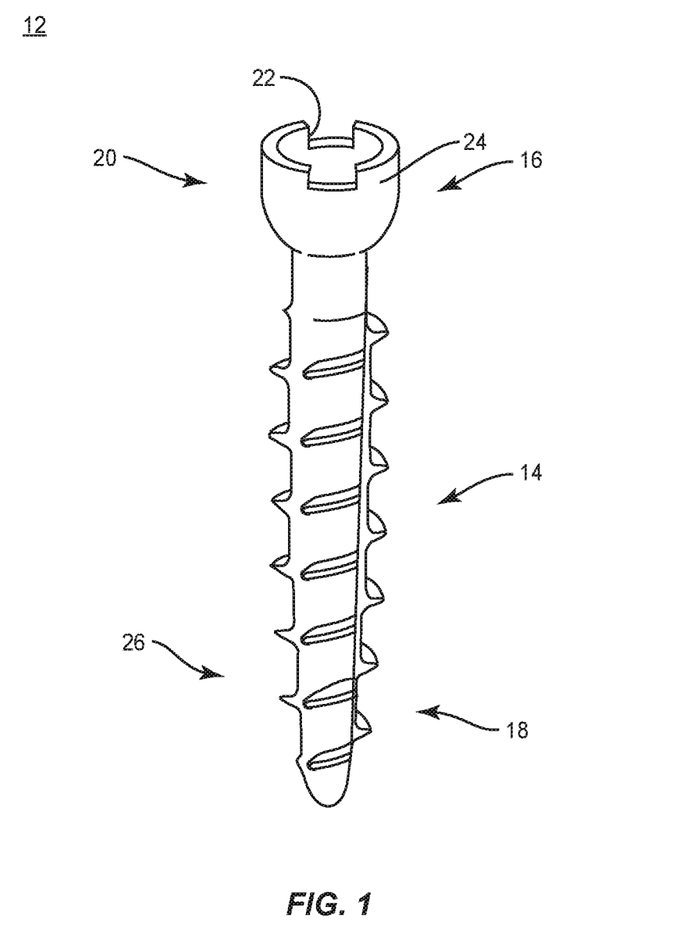
FIG. 1 is a perspective view of components of one embodiment of a surgical system in accordance with the principles of the present disclosure.

The following discussion includes a description of a surgical system including surgical instruments, spinal constructs, implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIG. 1, there is illustrated components of a surgical system, such as, for example, a spinal instrument system 10.

The components of spinal instrument system 10 can be fabricated from biologically acceptable materials suitable for medical applications, including metals, synthetic polymers, ceramics and bone material and/or their composites. For example, the components of spinal instrument system 10, individually or collectively, can be fabricated from materials such as stainless steel alloys, aluminum, commercially pure titanium, titanium alloys, Grade 5 titanium, super-elastic titanium alloys, cobalt-chrome alloys, super-elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

The components of spinal instrument system 10, individually or collectively, may also be fabricated from a heterogeneous material such as a combination of two or more of the above-described materials. The components of spinal instrument system 10 may be monolithically formed, integrally connected or include fastening elements and/or instruments, as described herein.

Spinal instrument system 10 can be employed, for example, with a minimally invasive procedure, including percutaneous techniques, mini-open and open surgical techniques to manipulate tissue, deliver and introduce instrumentation and/or components of spinal constructs at a surgical site within a body of a patient, for example, a section of a spine. In some embodiments, spinal instrument system 10 includes a surgical device, as described herein, which comprises one or more surgical instruments, which can be employed with surgical navigation and/or robotic guidance. In some embodiments, the surgical device provides marking and guidance with vertebral tissue, and vertebral manipulation to treat spinal disorders, for example, to manage lordosis and/or kyphosis restoration. In some embodiments, the surgical device provides a tissue tap for pilot holes, distraction and/or compression of vertebral tissue employed in connection with surgical treatment. In some embodiments, spinal instrument system 10 can include spinal constructs having, for example, interbody devices, interbody cages, bone fasteners, spinal rods, tethers, connectors, plates and/or bone graft. The surgical procedure can include surgical treatment of a cervical, thoracic, lumbar and/or sacral region of a spine. In some embodiments, spinal instrument system 10 is configured to distract tissue during a transforaminal lumbar interbody fusion (TLIF) procedure.

In some embodiments, spinal instrument system 10 includes a surgical device, as described herein, which comprises and/or is connectable with one or more surgical instruments, such as, for example, a driver, a cutter, a cannula, an osteotome, an inserter, a compressor and/or a distractor that can be employed with spinal implants. In some embodiments, the surgical device can be employed in connection with various access procedures to one or a plurality of surgical approaches for tissue tapping, marking guidance, compression/distraction maneuvers, leveraging vertebrae and/or, distributing loads across vertebrae.

Spinal instrument system 10 includes a surgical device that is configured as a surgical instrument 12. Surgical instrument 12 is configured to engage tissue of, for example, a pilot hole to create threads in tissue. Surgical instrument 12 is configured to mark a location and/or a trajectory for other surgical instruments and/or devices and/or spinal implants. In some embodiments, surgical instrument 12 comprises a tissue marker, for example, a pedicle marker instrument that provides guidance with vertebral tissue, bone tapping and/or manipulation of adjacent vertebrae of a spine. In some embodiments, surgical instrument 12 is employed to relatively rotate vertebrae for distraction and/or compression. In some embodiments, surgical device 12 is configured as a spinal implant and is employed as a provisional instrument.

Surgical instrument 12 includes a shaft 14. Shaft 14 extends between a proximal portion 16 and a distal portion 18. Portion 16 includes a head 20. Head 20 has a solid body and an end portion having a mating element, such as, for example, surfaces that define recesses 22 configured to facilitate engagement with a surgical instrument, as described herein. Portion 16 is configured for connection with one or a plurality of surgical instruments, as described herein, to facilitate manipulation of surgical instrument 12 and/or tissue. In some embodiments, head 20 can include a cylindrical or a spherical configuration. Head 20 or only a portion of head 20 may have cross section configurations, such as, for example, spherical, oval, oblong, triangular, square, polygonal, irregular, uniform, non-uniform, offset, staggered, undulating, arcuate, variable and/or tapered.

Head 20 comprises a detectable marker, for example, a pedicle marker 24, as shown in FIG. 1. Marker 24 is utilized to mark a location and/or a trajectory of a pedicle screw placement. In some embodiments, marker 24 includes an identifiable shape and/or configuration, for example, a cylindrical or spherical configuration, which is detectable visually and/or via imaging, as described herein. In some embodiments, head 20 comprises marker 24 having a radiopaque and/or radiographically detectable marker for visualizing a position and/or alignment of surgical instrument 12 using fluoroscopy during insertion, manipulation and implantation thereof. Marker 24 may be utilized for identification under x-ray, fluoroscopy, CT, MRI or other imaging techniques. In some embodiments, marker 24 can include indicia comprising identifying information relating to marker 24, a patient being treated and/or a medical procedure. In some embodiments, the indicia includes a memory device or data carrier, such as, for example, a RFID tag used in conjunction with an RFID system. In some embodiments, the indicia includes visual indicia, such as, for example, a label, color coding, numbers or an icon. In some embodiments, the indicia includes tactile indicia, such as, for example, raised portions, dimples and/or texturing.

Distal portion 18 has a cylindrical cross-sectional configuration and includes an outer surface having an external thread form. Distal portion 18 includes a solid configuration such that shaft 14 is non-cannulated, and surgical instrument 12 is employable in surgical applications without a guide wire. In some embodiments, portion 18 is configured to form an internal or female thread in tissue such that a spinal implant, such as, for example, a pedicle screw can be threaded into the internal thread formed by surgical instrument 12.

In some embodiments, the external thread form may include a single thread or a plurality of discrete threads. In some embodiments, other engaging structures may be located on portion 18, such as, for example, a nail configuration, barbs, expanding elements, raised elements and/or spikes to facilitate engagement of portion 18 with tissue. In some embodiments, all or only a portion of portion 18 may have alternate cross section configurations, such as, for example, oval, oblong, triangular, square, polygonal, irregular, uniform, non-uniform, offset, staggered, undulating, arcuate, variable and/or tapered. In some embodiments, all or only a portion of the outer surface of portion 18 may have alternate surface configurations to enhance fixation with tissue, such as, for example, rough, arcuate, undulating, mesh, porous, semi-porous, dimpled and/or textured. In some embodiments, all or only a portion of portion 18 may be disposed at alternate orientations, relative to its longitudinal axis, such as, for example, transverse, perpendicular and/or other angular orientations such as acute or obtuse, co-axial and/or may be offset or staggered.

Figure 8:
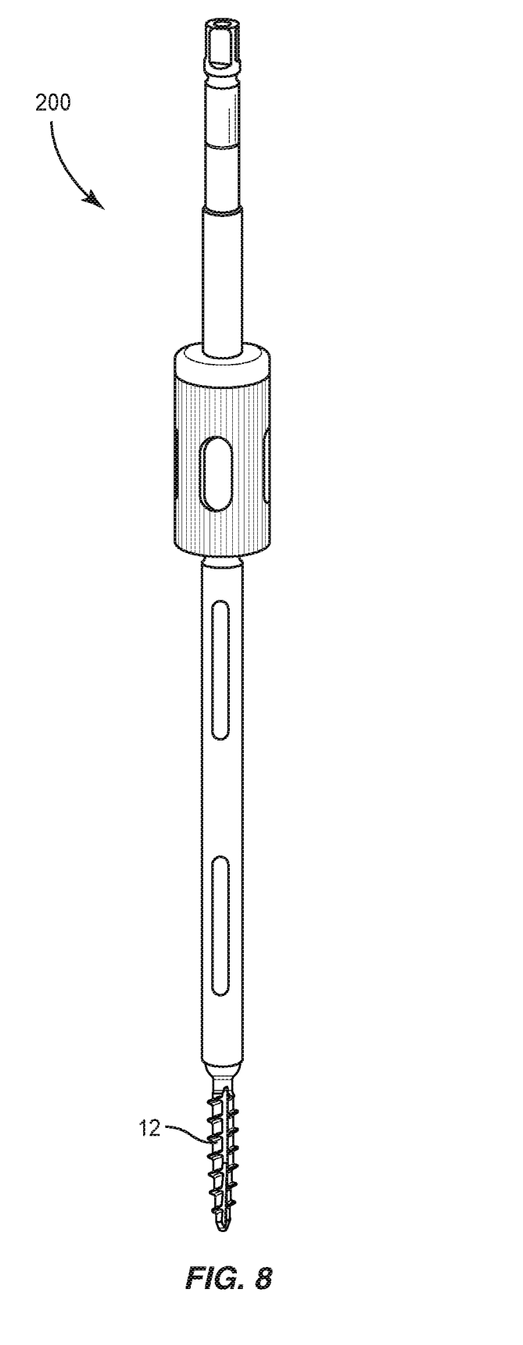
FIG. 8 is a perspective view of components of one embodiment of a surgical system in accordance with the principles of the present disclosure.

In some embodiments, surgical instrument 12 is engageable with a surgical instrument, such as, for example a driver 200, as shown in FIG. 8. Driver 200 is configured for connection with surgical instrument 12 to facilitate insertion and engagement with tissue. In some embodiments, driver 200 is configured for connection with an actuator, such as, for example, a motorized actuator, such as, for example, a powered drill (not shown). In some embodiments, driver 200 is actuated to cause surgical instrument 12 to create threads in vertebral tissue about a pilot hole.

Figure 2:
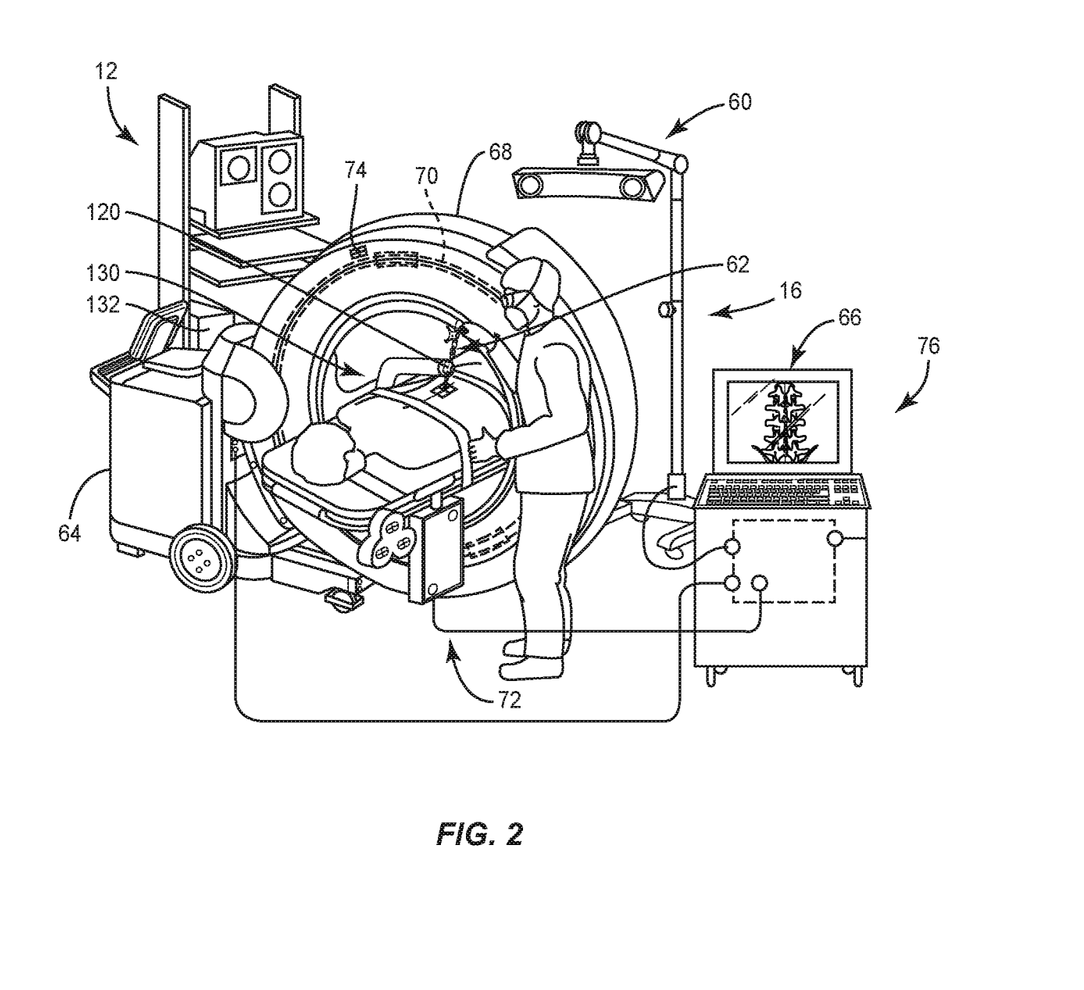
FIG. 2 is a plan view of components of one embodiment of a surgical system in accordance with the principles of the present disclosure.
Figure 3:
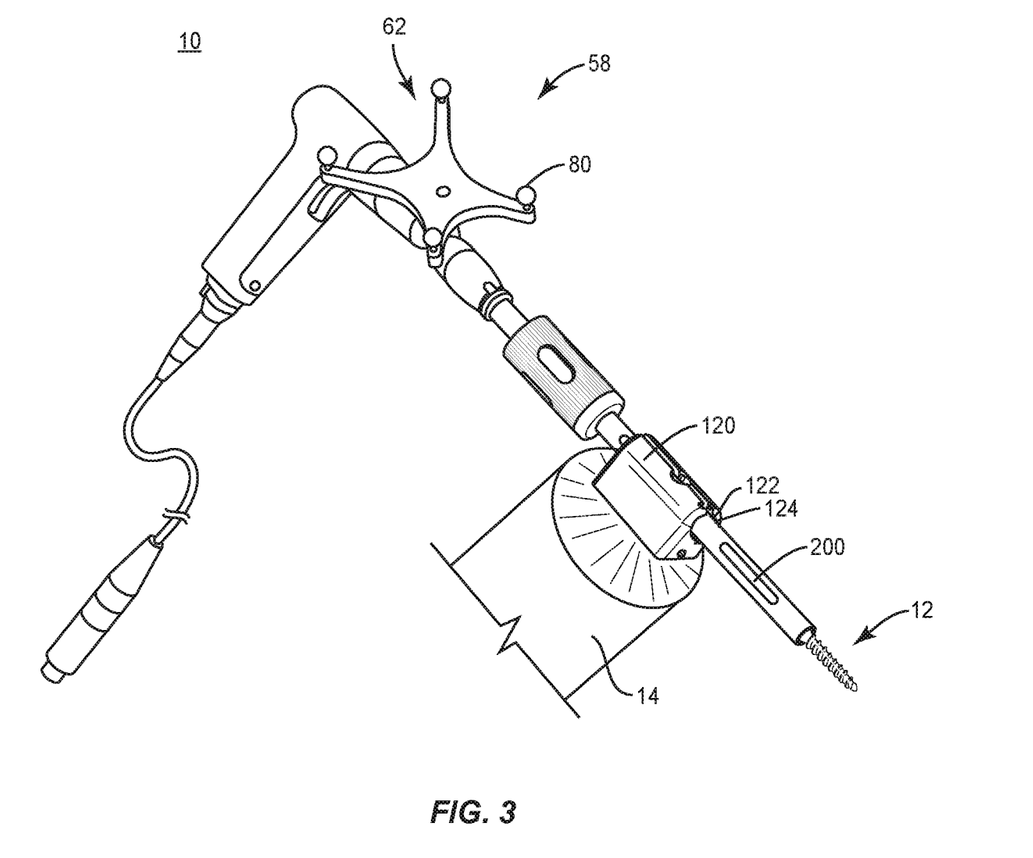
FIG. 3 is a perspective view of components of one embodiment of a surgical system in accordance with the principles of the present disclosure.

In some embodiments, driver 200 includes a navigation component 58 configured to generate a signal representative of a position of surgical instrument 12 relative to tissue. Surgical instrument 12 is configured for disposal adjacent a surgical site such that navigation component 58 is oriented relative to a sensor array 60, as shown in FIGS. 2 and 3, to facilitate communication between navigation component 58 and sensor array 60 during a surgical procedure, as described herein. Navigation component 58 is configured to generate a signal representative of a position of surgical instrument 12 and/or tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. In some embodiments, the navigation component is connected via an integral connection, friction fit, pressure fit, interlocking engagement, mating engagement, dovetail connection, clips, barbs, tongue in groove, threaded, magnetic, key/keyslot and/or drill chuck.

Navigation component 58 includes an emitter array 62. Emitter array 62 is configured for generating a signal to sensor array 60. In some embodiments, the signal generated by emitter array 62 represents a position of surgical instrument 12 relative to tissue, such as, for example, bone. In some embodiments, the signal generated by emitter array 62 represents a three-dimensional position of surgical instrument 12 relative to tissue. In some embodiments, emitter array 62 may include a reflector array configured to reflect a signal from sensor array 60.

In some embodiments, sensor array 60 receives signals from emitter array 62 to provide a three-dimensional spatial position and/or a trajectory of surgical instrument 12 relative to tissue. Emitter array 62 communicates with a processor of a computer 64 to generate data for display of an image on a monitor 66, as described herein. In some embodiments, sensor array 60 receives signals from emitter array 62 to provide a visual representation of a position of surgical instrument 12 relative to tissue. See, for example, similar surgical navigation components and their use as described in U.S. Pat. Nos. 6,021,343, 6,725,080, 6,796,988, the entire contents of each of these references being incorporated by reference herein.

In some embodiments, the navigation system comprises image capturing portion 70 that may include an x-ray source or emission portion and an x-ray receiving or image receiving portion located generally or as practically possible 180 degrees from each other and mounted on a rotor (not shown) relative to a track of image capturing portion 70. Image capturing portion 70 can be operable to rotate 360 degrees during image acquisition. Image capturing portion 70 may rotate around a central point or axis, allowing image data of the patient to be acquired from multiple directions or in multiple planes. The surgical navigation system can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, the surgical navigation system can include C-arm fluoroscopic imaging systems, which can generate three-dimensional views of a patient. The position of image capturing portion 70 can be precisely known relative to any other portion of an imaging device of the navigation system. In some embodiments, a precise knowledge of the position of image capturing portion 70 can be used in conjunction with a tracking system 72 to determine the position of image capturing portion 70 and the image data relative to the patient.

Tracking system 72 can include various portions that are associated or included with the surgical navigation system. In some embodiments, tracking system 72 can also include a plurality of types of tracking systems, such as, for example, an optical tracking system that includes an optical localizer, such as, for example, sensor array 60 and/or an EM tracking system that can include an EM localizer. Various tracking devices can be tracked with tracking system 72 and the information can be used by the surgical navigation system to allow for a display of a position of an item, such as, for example, a patient tracking device, an imaging device tracking device 74, and an instrument tracking device, such as, for example, emitter array 62, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

In some embodiments, the surgical navigation system provides for real-time tracking of the position of surgical instrument 12 relative to tissue. Sensor array 60 is located in such a manner to provide a clear line of sight with emitter array 62, as described herein. In some embodiments, fiducial markers 80 of emitter array 62 communicate with sensor array 60 via infrared technology. Sensor array 60 is coupled to computer 64, which may be programmed with software modules that analyze signals transmitted by sensor array 60 to determine the position of each object in a detector space.

Surgical instrument 12 is configured for use with an end effector 120 of a robotic arm 126. End effector 120 includes a surface 122 that defines a channel 124. Channel 124 is configured for passage and/or disposal of the components of surgical instrument 12 relative to tissue, as described herein. Robotic arm 126 includes position sensors (not shown), similar to those referenced herein, which measure, sample, capture and/or identify positional data points of end effector 120 in three dimensional space for a guide-wireless insertion of components of surgical instrument 12 relative to tissue, for example, with selected vertebral levels. In some embodiments, surface 122 comprises an axial trajectory guide configured for passage and/or disposal of the components of surgical instrument 12 relative to tissue, as described herein. In some embodiments, a sleeve, which comprises an axial trajectory guide, is connected with surface 122. In some embodiments, the position sensors of robotic arm 126 are employed in connection with the surgical navigation system to measure, sample, capture and/or identify positional data points of end effector 120 in connection with surgical treatment, as described herein. The position sensors are mounted with robotic arm 126 and calibrated to measure positional data points of end effector 120 in three dimensional space, which are communicated to the components of a surgical robotic guidance system and/or computer 64. See, for example, the surgical robotic guidance systems and methods described in U.S. Pat. No. 8,571,638, the contents of which being hereby incorporated by reference herein in its entirety.

The surgical robotic guidance system includes a surgical robot 130 including robotic arm 126, which positions one or more surgical instruments, as described herein, with respect to a surgical site and is employed with a method for using robot 130 to assist in surgical procedures, as shown in FIG. 2. In some embodiments, robot 130 attaches to patient anatomy, for example, bone with a clamp (not shown) or K-wires of robot 130. Robotic arm 126 extends and moves relative to a base of robot 130 to assist in surgical procedures. See, for example, the surgical robot configurations described in U.S. Pat. No. 8,571,638, the contents of which being hereby incorporated by reference herein in its entirety. In some embodiments, robot 130 is not physically connected with the patient anatomy, for example, a navigation system, as described herein, registers the patient anatomy with respect to the location of robot 130, which includes the location of the robot's end effector 120, such that robotic arm 126 extends and moves relative to the base of robot 130 to assist in surgical procedures.

In some embodiments, the surgical robotic guidance system includes a control unit 132 that matches data from CT scans and C-arm images to locate surgical robot 130 and allows a surgeon to control surgical robot 130, through the use of a mouse, joystick, touch screen, or the like; and monitor 66. In some embodiments, control unit 132 may include a central processing unit (CPU) and user interface communicating with monitor 66 and robot 130. Robot 130 aligns end effector 120 and surgical instrument 12 with a surgical site requiring a surgical procedure percutaneously, mini-open or in open procedures.

In assembly, operation and use, spinal instrument system 10, similar to the systems and methods described herein, is employed with a surgical procedure, such as, for example, a treatment of an applicable condition or injury of an affected section of a spinal column and adjacent areas within a body. In some embodiments, one or all of the components of spinal instrument system 10 can be delivered or utilized as a pre-assembled device or can be assembled in situ. Spinal instrument system 10 may be completely or partially revised, removed or replaced.

In use, to treat vertebrae V, a medical practitioner obtains access to a surgical site in any appropriate manner, such as through incision and retraction of tissues. In some embodiments, spinal instrument system 10 can be used in any existing surgical method or technique including open surgery, mini-open surgery, minimally invasive surgery and percutaneous surgical implantation, whereby vertebrae V1, V2 are accessed through a mini-incision, or sleeve that provides a protected passageway to the area. Once access to the surgical site is obtained, the particular surgical procedure can be performed for treating the spine disorder.

The surgical robotic guidance system includes intra-operative guidance such that a surgeon directs robot 130 to guide surgical instruments, as described herein, and implants at a trajectory and position. Robot 130 responds and moves end effector 120, which includes an axial trajectory guide, for example, channel 124 and/or a sleeve disposed with surface 122, into position, such that a surgical instrument disposed with end effector 120 can be aligned with a location. In some embodiments, the surgeon can insert a spinal construct component and/or surgical instrument with end effector 120 and visually verify positioning of the spinal construct component and/or surgical instrument from control unit 132 and/or monitor 66. In some embodiments, a surgeon can manipulate robot 86 by use of a joystick, mouse and/or touch screen.

Channel 124 of end effector 120 provides an axial guide for surgical instruments according to an implant strategy and/or a surgical pathway for delivery of components of spinal instrument system 10, which may include, such as, for example, drivers, extenders, reducers, spreaders, distractors, blades, clamps, forceps, elevators and drills, which may be alternately sized and dimensioned, and arranged as a kit. In some embodiments, the surgeon disposes a sleeve (not shown) with end effector 120, which provides an axial guide.

Figure 4:
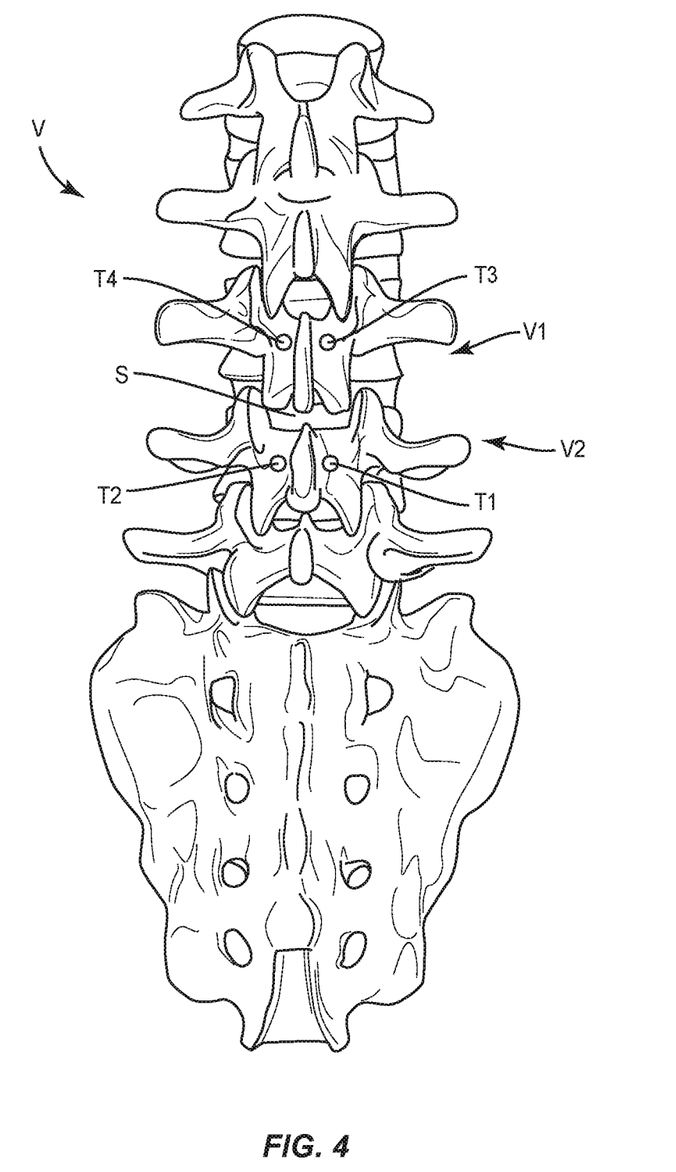
FIG. 4 is a plan view of one embodiment of an implant strategy in accordance with the principles of the present disclosure.
Figure 5:
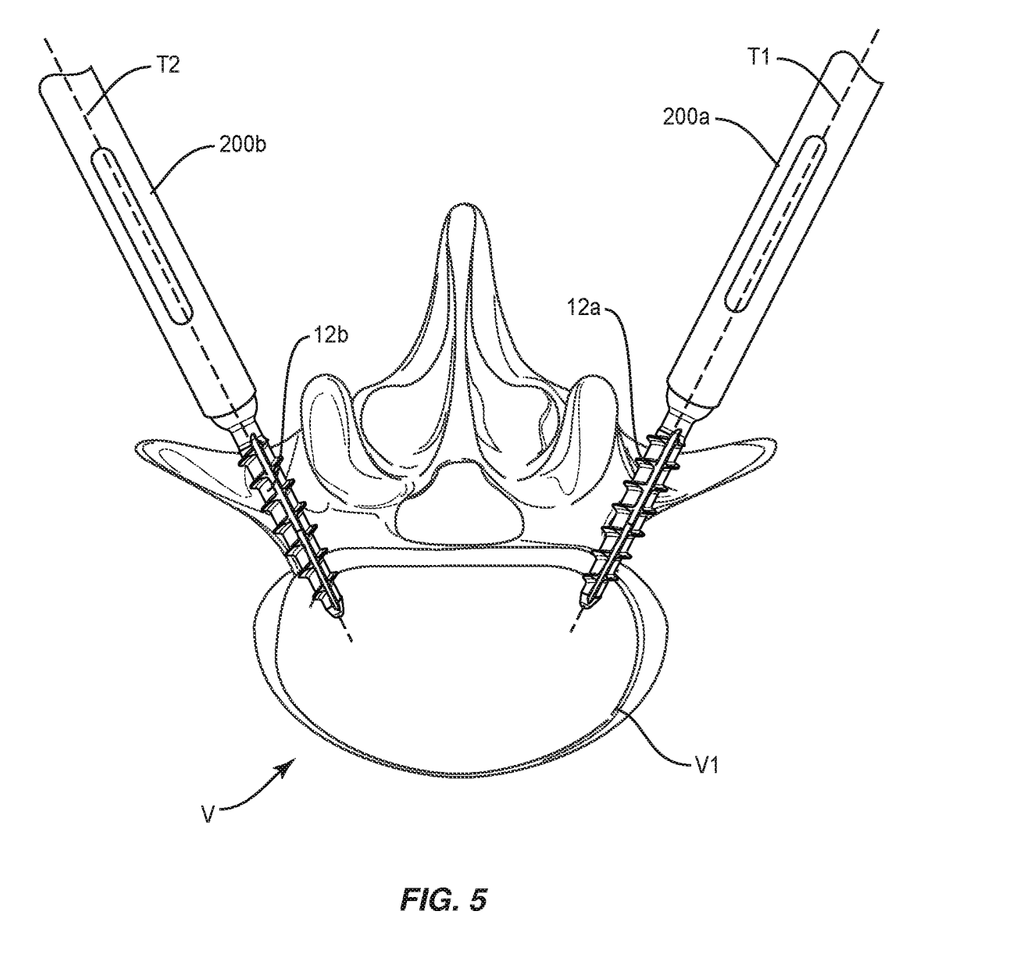
FIG. 5 is an axial view of components of one embodiment of a surgical system in accordance with the principles of the present disclosure disposed with vertebrae.
Figure 6:
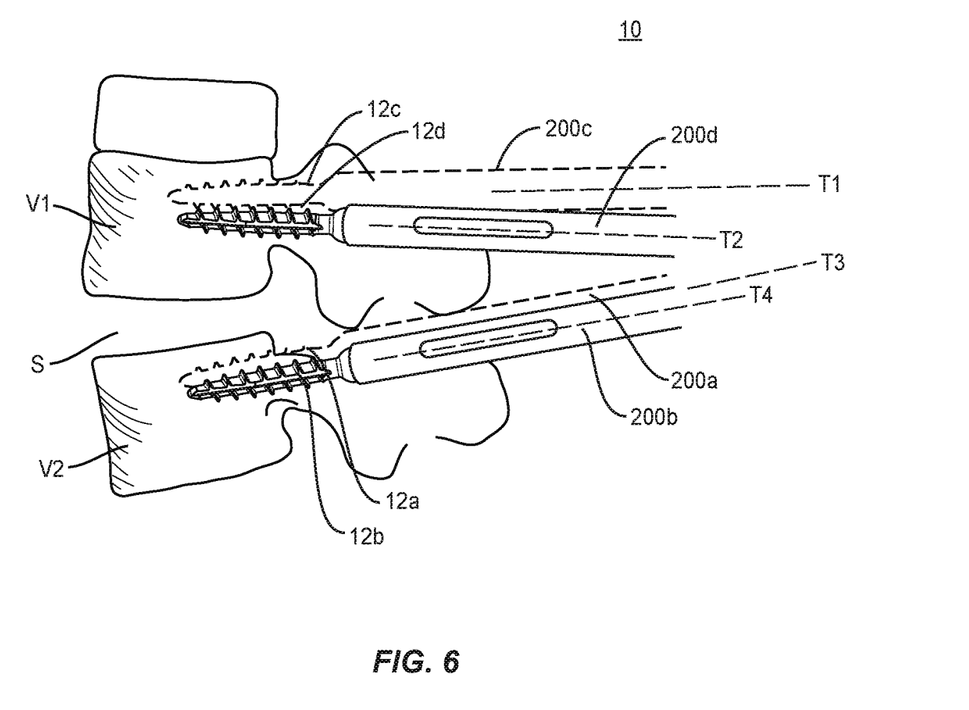
FIG. 6 is a side view of components of one embodiment of a surgical system in accordance with the principles of the present disclosure disposed with vertebrae.

For example, as shown in FIGS. 4-6, a surgical procedure includes selecting an implant trajectory T1 of an insertion path and positioning of a surgical instrument 12*a*, similar to surgical instrument 12 described herein, with a lateral side of a vertebra V1. Implant trajectory T1 includes an axial or linear pathway for delivering surgical instruments to a selected location of the lateral side of vertebra V1. In some embodiments, implant trajectory T1 includes delivering spinal construct components to a selected location of the lateral side of vertebra V1.

A surgeon moves robot 130 such that channel 124 is aligned with screw trajectory T1. In some embodiments, surface 122 of end effector 120 may be connected, attached or monolithically formed with a sleeve, cannula and/or dilator to define the surgical pathway along screw trajectory T1 to vertebra V1. A drill (not shown) is disposed within the surgical pathway. The drill is translated by the surgeon through channel 124 in alignment with screw trajectory T1. The drill is actuated to create a pilot hole in vertebra V1 along implant trajectory T1. The drill is removed from the surgical pathway.

A driver 200*a*, similar to driver 200 described herein, is connected with surgical instrument 12*a*, as described herein. Alignment of channel 124 with screw trajectory T1 is maintained and the surgeon positions surgical instrument 12*a* within the surgical pathway of channel 124. Surgical instrument 12*a* is translated by the surgeon along the surgical pathway in alignment with implant trajectory T1 and engaged with tissue of vertebra V1. With surgical instrument 12*a* engaged with the tissue of vertebra V1, for example, a pedicle, marker 24 is detected via imaging, as described herein, to confirm location and trajectory of surgical instrument 12*a*, for example, to confirm alignment with implant trajectory T1. Surgical instrument 12*a* is actuated for rotation to create threads in vertebra V1 about the pilot hole. In some embodiments, surgical instrument 12*a* remains engaged with vertebra V1 such that surgical instrument 12*a* provides guidance with vertebral tissue and/or manipulation of vertebrae V, as described herein. In some embodiments, surgical instrument 12*a* may be engaged with various portions of a vertebra, for example, anterior, posterior, interbody, intrabody, facet, laminae and/or one or more process.

In some embodiments, an implant trajectory T2 is selected of an insertion path and positioning of a surgical instrument 12*b*, similar to surgical instrument 12 described herein, with a contra-lateral side of vertebra V1, similar to implant trajectory T1 described herein, to create a pilot hole in vertebra V1 along screw trajectory T2. The surgeon moves robot 130 such that channel 124 is aligned with screw trajectory T2. The drill is disposed within the surgical pathway. The drill is translated by the surgeon through channel 124 in alignment with screw trajectory T2. The drill is actuated to create a pilot hole in vertebra V1 along implant trajectory T2. The drill is removed from the surgical pathway.

A driver 200b, similar to driver 200 described herein, is connected with surgical instrument 12b. Alignment of channel 124 with screw trajectory T2 is maintained and the surgeon positions surgical instrument 12b within the surgical pathway of channel 124. Surgical instrument 12b is translated by the surgeon along the surgical pathway in alignment with implant trajectory T2 and engaged with tissue of vertebra V1. With surgical instrument 12b engaged with the pedicle of vertebra V1, marker 24 is detected via imaging, as described herein, to confirm location and alignment of surgical instrument 12b with implant trajectory T2. Surgical instrument 12b is actuated for rotation to create threads in vertebra V1 about the pilot hole.

In some embodiments, an implant trajectory T3 is selected of an insertion path and positioning of a surgical instrument 12c, similar to surgical instrument 12 described herein, with a lateral side of vertebra V2, similar to implant trajectory T1 described herein, to provide guidance with vertebral tissue, tissue tapping and/or manipulation of vertebrae V, as described herein. In some embodiments, an implant trajectory T4 is selected of an insertion path and positioning of a surgical instrument 12d, similar to surgical instrument 12 described herein, with a contra-lateral side of vertebra V2, similar to implant trajectory T2 described herein, to provide guidance with vertebral tissue, tissue tapping and/or manipulation of vertebrae V, as described herein.

In some embodiments, spinal instrument system 10 is employed with a pedicle subtraction osteotomy (PSO) procedure for treatment of an applicable condition or injury of an affected section of a spinal column and adjacent areas within a body. A preparation instrument (not shown) is employed to remove disc tissue, fluids, adjacent tissues and/or bone, and scrape and/or remove tissue from endplate surfaces of vertebra V1 and/or endplate surface of vertebra V2. In some embodiments, vertebral facets are resected. A discectomy is performed to create vertebral space S between vertebral bodies V1, V2.

A compressor/distractor instrument, such as, for example, a distractor (not shown) is translated by the surgeon along the surgical pathway in alignment with screw trajectories T1, T3 for engagement with surgical instrument 12a/200a and surgical instrument 12c/200c, and connection with the lateral side of vertebrae V. A second distractor (not shown) is translated by the surgeon along the surgical pathway in alignment with screw trajectories T2, T4 for engagement with surgical instrument 12b/200b and surgical instrument 12d/200d, and connection with the contra-lateral side of vertebrae V. The connection of the distractors with the surgical instruments described herein facilitates lateral distraction and/or parallel distraction. Surgical instruments 12a-d remain engaged with vertebrae V1, V2 and connected to drivers 200 and the distractors to manipulate and/or relatively rotate selected vertebra of vertebrae V.

Each distractor is manipulated to axially translate an arm along a rack to facilitate compression and/or distraction of vertebrae V. The distractors selectively rotate surgical instruments 12a-d/200a-d to rotate vertebra V1 relative to vertebra V2 to decompress intervertebral space S between vertebrae V, relieve disc pressure, realign one or more vertebra and/or reduce compression on the spinal cord and adjacent nerves. In some embodiments, a spinal implant, such as, for example, an interbody implant (not shown) is disposed within intervertebral space S.

In some embodiments, one or more of surgical instruments 12a-d are configured as provisional instruments and are removed for engagement of permanent bone screws (not shown) with vertebrae V. In some embodiments, the permanent bone screws can be engaged with vertebrae V via the surgical robotic guidance system and similar to that described herein with regard to surgical instrument 12.

Figure 7:
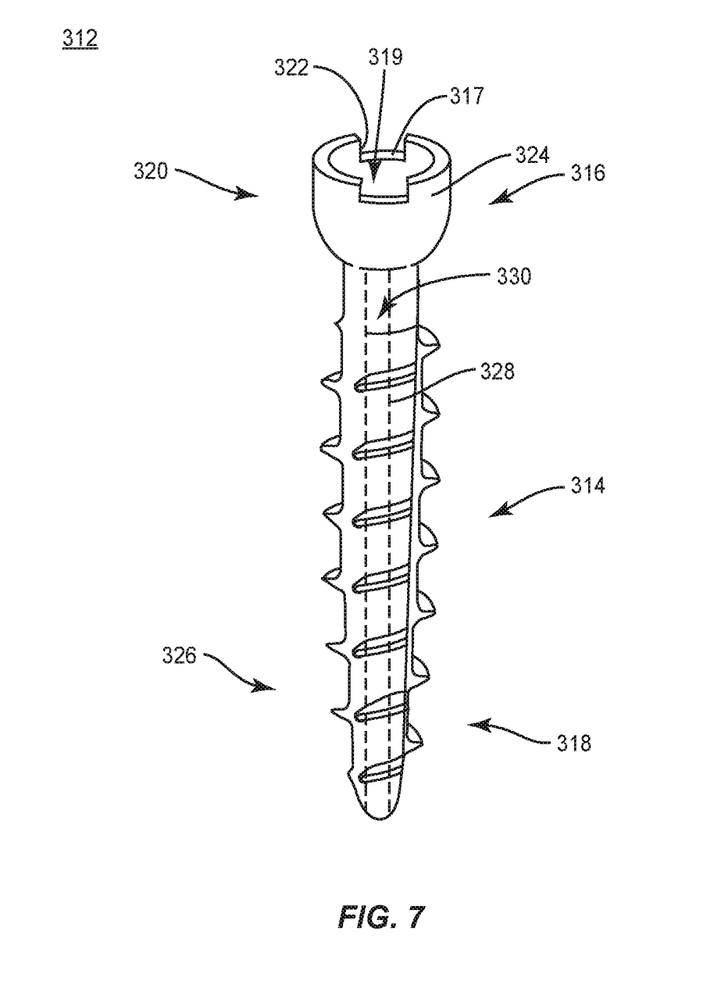
FIG. 7 is a perspective view of components of one embodiment of a surgical system in accordance with the principles of the present disclosure.

In one embodiment, as shown in FIG. 7, spinal instrument system 10, similar to the systems and methods described herein, includes a surgical instrument 312, similar to surgical instrument 12 described herein. Surgical instrument 312 includes a shaft 314. Shaft 314 extends between a proximal portion 316 and a distal portion 318. Portion 316 includes a head 320. Head 320 includes a surface 317 that defines an opening 319. Opening 319 is disposed in communication with a passageway 330. In some embodiments, head 320 can include a cylindrical or a spherical configuration. In some embodiments, head 320 includes a mating element, such as, for example, surfaces that define recesses 322 configured to facilitate engagement with a surgical instrument, as described herein. Portion 316 is configured for connection with one or a plurality of surgical instruments, as described herein, to facilitate manipulation of surgical instrument 312 and/or tissue. Head 320 comprises a detectable marker, for example, a pedicle marker 324, similar to that described herein. Marker 324 is utilized to mark a location and/or a trajectory of a pedicle screw placement.

Distal portion 318 has a cylindrical cross-sectional configuration and includes an outer surface having an external thread form. In some embodiments, portion 318 is configured to form an internal or female thread in tissue such that a spinal implant, such as, for example, a pedicle screw can be threaded into the internal thread formed by surgical instrument 312.

Figure 9:
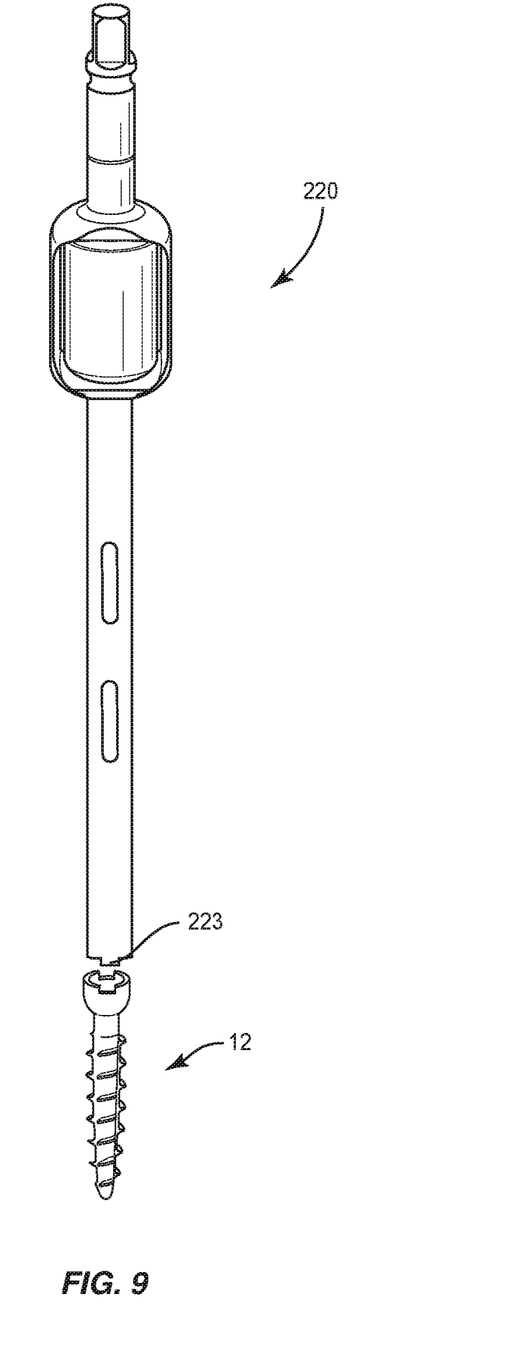
FIG. 9 is a perspective view of components of one embodiment of a surgical system in accordance with the principles of the present disclosure.

Portion 318 includes an inner surface 328 that defines a cavity, such as, for example, a passageway 330 forming a cannulated shaft 314. In some embodiments, passageway 330 is configured for disposal of a surgical tool, such as, for example, a guide wire to facilitate minimally invasive procedures. In one embodiment, surgical instrument 312 is employed with driver 200, as shown in FIG. 8, and similar to that described herein with regard to surgical instrument 12. In some embodiments, surgical instrument 12, and similarly surgical instrument 312, is employed with a driver 220, as shown in FIG. 9, which includes tabs 223 configured for engagement with recesses 22 of surgical instrument 12 in an external connection with surgical instrument 12.

In some embodiments, spinal instrument system 10 may include one or a plurality of spinal constructs. In some embodiments, the spinal constructs may be disposed in various alternate orientations, such as, for example, side by side, parallel, transverse and/or other angular orientations such as acute or obtuse, co-axial and/or may be offset or staggered. In some embodiments, the spinal constructs including spinal rods may provide a template configuration for permanently implantable spinal rods, such as, implantable, final, permanent, removable, non-removable, bio-absorbable, resorbable and/or bio-degradable, and/or comprise permanently implantable spinal rods.

Upon completion of a procedure, the surgical instruments and non-implanted components of spinal instrument system 10 are removed and the incision(s) are closed. One or more of the components of spinal instrument system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal instrument system 10.

In some embodiments, spinal instrument system 10 includes an agent, which may be disposed, packed, coated or layered within, on or about the components and/or surfaces of spinal instrument system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical device comprising:
   a surgical robot guide;
   a driver coupled to the surgical robot guide, the surgical robot guide being configured to move the driver relative to a patient; and
   a screw comprising a shaft extending along a longitudinal axis between a proximal portion and a distal portion, the proximal portion being coupled to driver to engage vertebral tissue and rotate the screw relative to the surgical robot guide, the driver being configured to generate a signal representative of a position of the screw, the distal portion comprising a helical thread and a flute extending parallel to the longitudinal axis through the thread, the proximal portion being monolithically formed with the distal portion and defining a detectable marker, the proximal portion comprising a wall having an inner surface and a proximal surface, the wall extending circumferentially about the longitudinal axis from the proximal surface to the distal portion, the proximal portion including first and second arms each extending proximally from the proximal surface, a first end of the first arm being spaced apart from a first end of the second arm by a first recess, a second end of the first arm being spaced apart from a second end of the second arm by a second recess, the inner surface of the wall and inner surfaces of the arms defining a non-threaded cavity, the cavity having a first depth along the longitudinal axis and the recesses each have a second depth along the longitudinal axis, the first depth being greater than the second depth.

2. A surgical device as recited in claim 1, wherein the detectable marker provides an image of the shaft relative to tissue.

3. A surgical device as recited in claim 1, wherein the detectable marker provides a location and/or trajectory for a spinal implant.

4. A surgical device as recited in claim 1, wherein the surgical robot guide includes an axial trajectory guide.

5. A surgical device as recited in claim 4, wherein the axial trajectory guide is configured for robotic guidance according to an implant strategy.

6. A surgical device as recited in claim 1, wherein the proximal portion includes a radiographically detectable marker.

7. A surgical device as recited in claim 1, wherein the first recess is aligned with the second recess along a transverse axis that extends perpendicular to the longitudinal axis.

8. A surgical device as recited in claim 1, wherein the first arm comprises a proximal surface extending continuously from the first end of the first arm to the second end of the first arm and the second arm comprises a proximal surface extending continuously from the first end of the second arm to the second end of the second arm, the proximal surfaces of the arms extending parallel to the proximal surface of the wall.

9. A surgical device as recited in claim 1, wherein the arms are each free of any recesses.

10. A surgical device as recited in claim 1, wherein the cavity is concave.

11. A surgical device as recited in claim 1, wherein the wall has a cylindrical cross-sectional configuration.

12. A surgical device as recited in claim 1, wherein the shaft is monolithic.

13. A method for treating a spine, the method comprising the steps of:
    engaging a screw with vertebral tissue via robotic guidance, the screw comprising a distal portion including a helical thread and a flute extending through the thread, the screw including a proximal portion including a detectable marker, the screw extending along a longitudinal axis between the distal portion and the proximal portion, the flute extending parallel to the longitudinal axis, the proximal portion being monolithically formed with the distal portion and comprising a wall having an inner surface and a proximal surface, the wall extending circumferentially about the longitudinal axis from the proximal surface to the distal portion, the proximal portion including first and second arms each extending proximally from the proximal surface, a first end of the first arm being spaced apart from a first end of the second arm by a first recess, a second end of the first arm being spaced apart from a second end of the second arm by a second recess, the inner surface of the wall and inner surfaces of the arms defining a non-threaded cavity, the cavity having a first depth along the longitudinal axis and the recesses each have a second depth along the longitudinal axis, the first depth being greater than the second depth;
    connecting a driver to the surgical robot guide;
    connecting the proximal portion to the driver;
    moving the driver relative to a patient using the surgical robot guide;
    rotating the screw using the driver such that the screw rotates relative to the surgical robot guide, the driver being configured to generate a signal representative of a position of the screw; and
    manipulating the surgical instrument to rotate a first vertebra of the vertebral tissue relative to a second vertebra.

14. A method as recited in claim 13, wherein the step of manipulating includes decompressing the vertebrae.

15. A method as recited in claim 13, wherein the screw includes a radiopaque marker and further comprising the step of imaging the screw with the vertebral tissue.

16. A method as recited in claim 15, further comprising the step of determining a location and/or trajectory for a spinal implant via the imaging.

17. A method as recited in claim 13, wherein the screw includes a cannulated shaft.

18. A method as recited in claim 13, further comprising the step of inserting an interbody implant between the vertebrae.

19. A surgical device comprising:

a screw extending along a longitudinal axis between a distal portion and a proximal portion, the distal portion comprising a helical thread and a flute extending along the longitudinal axis through the thread along an entire length of the thread, the proximal portion comprising a wall having an inner surface and a proximal surface, the wall extending circumferentially about the longitudinal axis from the proximal surface to the distal portion, the proximal portion being monolithically formed with the distal portion and including first and second arms each extending proximally from the proximal surface, a first end of the first arm being spaced apart from a first end of the second arm by a first recess, a second end of the first arm being spaced apart from a second end of the second arm by a second recess, the inner surface of the wall and inner surfaces of the arms defining a non-threaded cavity, the inner surface of the wall being continuous with the inner surfaces of the arms, the cavity having a first depth along the longitudinal axis and the recesses each have a second depth along the longitudinal axis, the first depth being greater than the second depth, at least a portion of the cavity having a circular-cross-sectional configuration;

a driver; and a surgical robot guide coupled to the driver, the surgical robot guide being configured to move the driver relative to a patient, the driver being configured to generate a signal representative of a position of the screw, the driver being configured to rotate the screw relative to the surgical robot guide, the driver comprising a shaft having a distal surface and spaced first and second tabs each extending distally from the distal surface, the first tab being disposed in the first recess and the second tab being disposed in the second recess to connect the driver with the screw.

20. A surgical device as recited in claim 19, wherein proximal surfaces of the arms directly engage the distal surface when the tabs are disposed in the recesses.

* * * * *